United States Patent
Koverech et al.

(10) Patent No.: US 8,343,979 B2
(45) Date of Patent: Jan. 1, 2013

(54) USE OF ALKANOYL L-CARNITINE FOR THE TREATMENT OF ERECTILE DYSFUNCTION

(75) Inventors: Aleardo Koverech, Pomezia (IT); Andrea Lenzi, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 13/280,749

(22) Filed: Oct. 25, 2011

(65) Prior Publication Data

US 2012/0041005 A1   Feb. 16, 2012

Related U.S. Application Data

(60) Continuation of application No. 11/649,796, filed on Jan. 5, 2007, now abandoned, which is a division of application No. 10/497,498, filed as application No. PCT/IT02/00758 on Dec. 4, 2002, now abandoned.

(30) Foreign Application Priority Data

Dec. 4, 2001 (IT) .............................. RM2001A0708

(51) Int. Cl.
*A01N 43/90* (2006.01)
*A61K 31/519* (2006.01)

(52) U.S. Cl. .................................................. 514/262.1

(58) Field of Classification Search ................ 541/262.1
See application file for complete search history.

(56) References Cited

U.S. PATENT DOCUMENTS

| | | | |
|---|---|---|---|
| 4,268,524 A | 5/1981 | Cavazza | |
| 5,811,457 A | 9/1998 | Corsi | |
| 6,037,373 A | 3/2000 | De Simone | |
| 6,133,281 A | 10/2000 | Gonzalez-Cadavid et al. | |
| 6,241,471 B1 | 6/2001 | Herron | |
| 2004/0087515 A1 | 5/2004 | Butler et al. | |

FOREIGN PATENT DOCUMENTS

| | | |
|---|---|---|
| WO | 99/03364 A | 1/1999 |
| WO | 01/26666 A | 4/2001 |

OTHER PUBLICATIONS

Lipshultz, et al., "Treatment of erectile dysfunction in men with diabetes." JAMA. 1999:281:465-46.

Goldstein et al., "Oral sildenafil in the treatment of erectile dysfunction." N. Engl. J Med 1998:338:1397-1404.

Gentile et al., "Preliminary Observations on the Use of Propionyl-L-Carnitine in Combination with Sildenafil in Patients with Erectile Dysfunction and Diabetes." Current Medical Research and Opinions, vol. 20, No. 9, 2004, 1377-1384.

Gaimmusso et al. "Improved Pallesthetic Sensitivity of Pudenal Nerve in Impotent Diabetic Patients Treated with Acetyl-LCarnitine." Acta URL et al, vol. 10, No. 3, 1996, pp. 185-187, XP001121375.

Cavallini et al., "Oral Propionyl-L-carnitine and Intraplaque verapamil in the Therapy of Advanced and Resistant Peyronie's Disease." BJU International, Blackwell Science, Oxford, GB, vol. 89, No. 9, Jun. 2002, pp. 895-900, XP001146228.

Goodman & Gilman's The Pharmaceutical Basis of Therapeutics, Ninth Edition, pp. 228-229. 1996.

*Primary Examiner* — Daniel Sullivan
*Assistant Examiner* — Trevor Love
(74) *Attorney, Agent, or Firm* — Lucas & Mercanti, LLP

(57) ABSTRACT

Erectile dysfunction is treated with a combination of propionyl L-carnitine in combination with sildenafil, apomorphine prostaglandin El, pentolamine and papaverine.

1 Claim, No Drawings

USE OF ALKANOYL L-CARNITINE FOR THE TREATMENT OF ERECTILE DYSFUNCTION

CROSS-REFERENCE TO RELATED APPLICATIONS

This application is a continuation application of U.S. Ser. No. 11/649,796 filed Jan. 5, 2007, which is a divisional of application Ser. No. 10/497,498 filed Jun. 3, 2004, now abandoned, which is the US national phase of international application PCT/IT02/00758 filed On 4 Dec. 2002, which claims priority to IT Application No. RM2001A000708 filed 4 Dec. 2001, contents of all of which are incorporated herein by reference.

The present invention relates to the use of an alkanoyl L-carnitine for the treatment of the erectile dysfunction.

The erectile dysfunction (E.D.) is a syndrome characterised by a persistent inability to obtain or maintain a penis erection, for a time sufficient for a sexual intercourse.

The current knowledge indicates that the relaxation of the smooth musculature of the corpus cavernosum which is necessary for the erection is due to a non adrenergic, non cholinergic mechanism, mediated by nitric oxide (ON), in which prostaglandin (PO) is involved (Medicina Pratica, 2000; 12-16).

The relaxation of the smooth musculature of the corpus cavernosum and the penis erection depend on a fine equilibrium between the effects of vasoconstrictor and vasodilator factors.

To bring the penis to erection, it is necessary that the relaxation of the smooth musculature of the corpus cavernosum exceeds a determined minimum level [Cardiovasc. Drugs Ther. 1991; 5 Supp (1):77-83].

It has been shown that the basic defect in patients suffering from (E.D.) may be, independently from the actiology, an imbalance between the contraction and the capacity of the relaxation of the corpus cavernosum smooth musculature.

If the base tone of the corpus cavernosum smooth musculature is too high, the maximum relaxation level may not be sufficient to permit an haematic flux sufficient for a normal erection.

If a minimum level of relaxation of the smooth musculature is not reached or maintained, the resistance to the venous runoff due to the intracavernous haematic pressure and the consequent compression of the veins will be insufficient for a normal erection.

In patients suffering from diabetes mellitus, the onset of an autonomic neuropathy is the main cause of the loss of the cholinergic activation during the erectile process, with consequent reduction of the ON and prostaglandin release, furthermore, a reduced function of the noradrenergic nervous ending could arise leading to a decrease of the vasodilator neurotransmitter levels such as the Vasoactive Intestinal Peptides (VIP).

In fact, it is recognised the role of the autonomic activation linked to a sexual excitation which leads to the release of nitric oxide (ON) and prostaglandin ($PGI_2$) exerted by the endothelium of the tissue cavernous of the penis as response to a cholinergic activation (Fed. Proc. 1982; 41, 2858-62).

ON and PG activate a second messenger the cGMP (guanosin mono phosphate cyclic) which mediates a relaxant effect of the smooth muscle in the trabecules of the cavernous tissue, thus permitting the haematic flux to fill the sinuses and lead to the penis tumefaction.

The exact contrary occurs under the effect of the adrenalin activity through the ($\alpha_t$) adrenergic nervous endings In particular in the study of the E.D. in diabetes mellitus it has been demonstrated that an endothelial impairment is responsible for the decreased "relaxation" of the trabecular smooth musculature of the corpus cavernosum which, in normal conditions, is mediated by the ON and that is the base of the organic impotence.

It has been demonstrated that about 90% of patients suffering from Type II diabetes mellitus show an E.D. [Diabetologia 2001, Oct. 44, (10), 1296-1301].

Previous uses of alkanoyl L-carnitines are already known.

In U.S. Pat. No. 5,811,457 the use of propionyl L-carnitine for treating chronic obliterant arteriopathy is described.

In U.S. Pat. No. 6,063,820 the use of alkanoyl L-carnitines for preparing a therapeutical nutritional composition for individuals suffering from diabetes mellitus is described.

In WO99/06039 the use of L-carnitine or an alkanoyl L-carnitine in combination with long chain aliphatic alcohols useful for the prevention and treatment of pathologies due to an altered lipid metabolism and an higher platelet aggregation is described.

Further patents and publications describe the use of alkanoyl L-carnitines for therapeutical scopes, but none of these publications describe or suggest the use of an alkanoyl L-carnitine, alone or in combination with other compounds, for treating the erectile dysfunction.

Compounds useful for treating erectile dysfunction are already known. For example, in Int. Urol. Nephrol 2001; 32 (3), 403-7 the use of sildenafil for treating erectile dysfunction is described.

In Diabetologia 2001, Oct. 44, (10), 1296-1301 the use of sildenafil for treating erectile dysfunction in patients suffering from Type II diabetes mellitus is described.

In Salute Europa of Jun. 11, 2001 have been presented the first data (published in British Journal of Urology) relating to an Italian and European clinical trial using sub-lingual apomorphine, for treating erectile dysfunction.

Further publications describe the use of compounds useful for treating erectile dysfunction, but none of them describe or suggest the use of these compounds in combination with an alkanoyl L-carnitine, for treating said pathology.

Known compounds useful for treating the E.D. are not free of disadvantage.

For example, in Eur. Urol. 2001 Aug; 40 (2) : 176-80 it is reported that not all patients respond to the treatment with sildenafil.

In Diabetologia 2001 Oct; 44 (10) : 1296-301 it is reported that not all diabetic patients respond to the treatment with sildenafil.

In Salute Europa of Jun. 11, 2001, it is reported that not all patients affected by E.D. treated with apomorphine respond to this treatment.

In Hosp. Med. 1998 Oct; 59 (10): 777 and in Br. J. Urol. 1996 Oct; 78(4): 628-31 it is reported that the administration of prostaglandin El and of papaverine, respectively, is carried out intracavernously, and it is well known how troublesome is this way of administration.

The need to have new drugs, useful for the treatment of the erectile dysfunction, which do not present the disadvantages of the known drugs, is therefore very much felt.

It has now been found that the alkanoyl L-carnitines wherein the alkanoyl group, linear or branched, has 2-6 carbon atoms, or a pharmaceutically acceptable salt thereof are useful agents for treating the erectile dysfunction.

What is meant by pharmacologically acceptable salt of an alkanoyl L-carnitine is any salt of the latter with an acid that does not give rise to unwanted toxic or side effects.

These acids are well known to pharmacologists and to experts in pharmacy.

Non-limiting examples of pharmacologically acceptable salts of alkanoyl L-carnitines are chloride, bromide, orotate, acid aspartate, acid citrate, magnesium citrate, acid phosphate, fumarate and acid fumarate, magnesium fumarate, lactate, maleate, acid maleate, mucate, acid oxalate, pamoate, acid pamoate, acid sulphate, glucose phosphate, tartrate, acid tartrate, magnesIum tartrate, 2-amino ethan sulphonate, magnesium 2-amino etansulphonate, Choline tartrate and trichloroacetate.

Non-limiting examples of alkanoyl L-carnitines are acetyl, propionyl, butyryl, isobutyryl, valeryl and isovaleryl L-carnitine.

Preliminary experimental data related to the use of propionyl L-carnitine, have shown that this compound is useful for treating the erectile dysfunction, in diabetics or in nondiabetics patients, not previously treated with sildenafil.

It is therefore an object of the present invention the use of propionyl L-carnitine, or a pharmaceutical acceptable salt thereof, for preparing a medicine for the treatment of erectile dysfunction.

A further object of the present invention is the use of propionyl L-carnitine for preparing a medicine for the treatment of erectile dysfunction in patients suffering from diabetes mellitus.

In the medical field it is known that specific drugs for treating E.D. which show not to be active (when used alone) on a particular group of patients in need of such drugs, they become active if combined between them (Br. J. Urol 1996 May; 77(5): 736-9).

The following experimental data show that the compounds according to the present invention are suitable to be used in combination with further drugs useful for treating E.D.

According to the present invention by "useful drugs" it is intended any drug useful for treating E.D.

It is therefore an object of the present invention the combination of an alkanoyl L-carnitine with one or more drugs useful for treating erectile dysfunction.

A further object of the present invention are pharmaceutical compositions comprising as active ingredient an alkanoyl L-carnitine in combination with one or more of said useful drugs, and at least an excipient and/or diluent pharmaceutically acceptable.

Non-limiting examples of said useful drugs are sildenafil, apomorphine, prostaglandin El, pentolamine or papaverine.

A further object of the present invention is the use of an alkanoyl L-carnitine, or a pharmaceutical acceptable salt thereof, in combination with one or more of said useful drugs, for preparing a medicine for the treatment of erectile dysfunction.

A further object of the present invention is the use of an alkanoyl L-carnitine in combination with one or more of said useful drugs, for preparing a medicine for the treatment of erectile dysfunction in patients affected by diabetes mellitus.

A further object of the present invention is the use of an alkanoyl L-carnitine in combination with one or more of said useful drugs, for preparing a medicine for the treatment of erectile dysfunction, wherein said patients do not respond to the treatment with said useful drugs.

A further object of the present invention is the use of an alkanoyl L-carnitine in combination with one or more of said useful drugs, for preparing a medicine for the treatment of erectile dysfunction in patients suffering from diabetes mellitus, wherein said patients do not respond to the treatment with said useful drugs.

Also in these further aspects of the present invention propionyl L-carnitine is preferred.

The alkanoyl L-carnitines and the useful drugs above mentioned can be prepared for a simultaneous, sequential or separated administration.

Though the daily dose will depend, according to the judgement of the primary care physician, on the patient's weight, age and general condition, it is generally advisable to administer 0.5 to 4 g/die of alkanoyl L-carnitine or a stoichiometrically equivalent amount of one of its pharmacologically acceptable salts. 1-2 g/die are preferred.

Larger doses can be administered in view of the alkanoyl L-carnitines substantial lack of toxicity.

Also the of administration regimen of the two active ingredients will depend on the primary care physician's judgement, the patient's weight, age and general conditions, it is generally advisable to administer the alkanoyl L-carnitine daily and said combined useful drug twice weekly.

The following examples illustrate the invention.

EXAMPLE 1

In this trial, 24 diabetics patients suffering from E.D. which were not responder to the treatment with sildenafil alone were enrolled.

2 g/day (1 g tablet twice a day) of propionyl L-carnitine were orally administered daily to the patients, and 50 mg sildenafil orally, twice a week.

After 3 and 6 months from the beginning of the treatment controls were made using the dynamic colour Doppler ultrasonography, these controls showed an improvement of the arterial flux which was coincident with a satisfactory clinical response evaluated with IIEF (Urology 1997 Jun;49(6):822-30) in 60% of treated patients.

EXAMPLE 2

In this trial, 30 diabetics patients suffering from E.D. which were not responder to the treatment with sildenafil alone were enrolled.

2 g/day (1 g tablet twice a day) of propionyl L-carnitine, were orally administered daily to the patients, and 50 mg sildenafil orally, twice a week.

After 3 and 6 months from the beginning of the treatment controls were made using the dynamic colour Doppler ultrasonography, these controls showed an improvement of the arterial flux which was coincident with a satisfactory clinical response evaluated with IIEF in 60% of treated patients.

The invention claimed is:

1. A method of treating erectile dysfunction, which comprises administering to a patient in need thereof a composition consisting of 0.5 to 4 mg of propionyl L-carnitine and 50 mg of sildenafil.

* * * * *